United States Patent [19]
Kledzik et al.

[11] 4,384,193
[45] May 17, 1983

[54] INCUBATING DEVICE FOR SPECIMEN MOUNTED ON GLASS SLIDES IN IMMUNOASSAYS

[75] Inventors: Gary S. Kledzik, Thousand Oaks; Glenn A. Wilson, Carpinteria; Mark D. Mahone, Goleta, all of Calif.

[73] Assignee: Immulok, Inc., Carpinteria, Calif.

[21] Appl. No.: 271,831

[22] Filed: Jun. 9, 1981

[51] Int. Cl.³ ............................................... H05B 3/06
[52] U.S. Cl. ..................................... 219/521; 119/37; 128/1 B; 219/385; 219/439; 219/530; 236/3; 237/3; 435/809
[58] Field of Search ............... 219/385, 430, 439, 521, 219/524, 525, 530, 540; 119/35, 37; 236/2, 3, 4, 236/5; 237/3, 14, 15; 435/290, 299, 300, 310, 316, 435/809; 128/1 B; 165/104

[56] References Cited

U.S. PATENT DOCUMENTS

| | | | |
|---|---|---|---|
| Re. 27,756 | 9/1973 | Martin | 435/809 X |
| 2,932,718 | 4/1960 | Marsters | 219/521 |
| 3,109,084 | 10/1963 | Walsh | 219/385 |
| 3,418,919 | 12/1968 | Nardon | 219/524 X |
| 3,714,885 | 2/1973 | Wertheimer | 219/524 X |
| 3,801,467 | 4/1974 | Nobe et al. | 435/809 X |
| 4,011,431 | 3/1977 | Levin | 219/524 |
| 4,308,447 | 12/1981 | Notzold et al. | 219/530 X |

Primary Examiner—Volodymyr Y. Mayewsky
Attorney, Agent, or Firm—Gabor L. Szekeres; Howard J. Klein

[57] ABSTRACT

An incubating device particularly adapted for aligning an array of microscope slides bearing a tissue section, sample or specimen, and incubating the same with a series of test or reagent solutions at a higher-than-ambient temperature, is disclosed. The incubating device has a main body including a recess which substantially forms a tray in the main body. A plurality of substantially regularly spaced metal blocks are disposed in the recess, and a substantially flat upper surface of each metal block is adapted to receive and be in contact with a respective microscope slide.

A heater is mounted underneath the main body to heat the main body, and to affect by direct conductance of heat, the heating of the metal blocks. A thermostat is mounted to the main body to monitor the temperature of the main body and to regulate the output of the heater in response thereto whereby the temperature of the metal blocks is maintained in a desired predetermined range.

14 Claims, 4 Drawing Figures

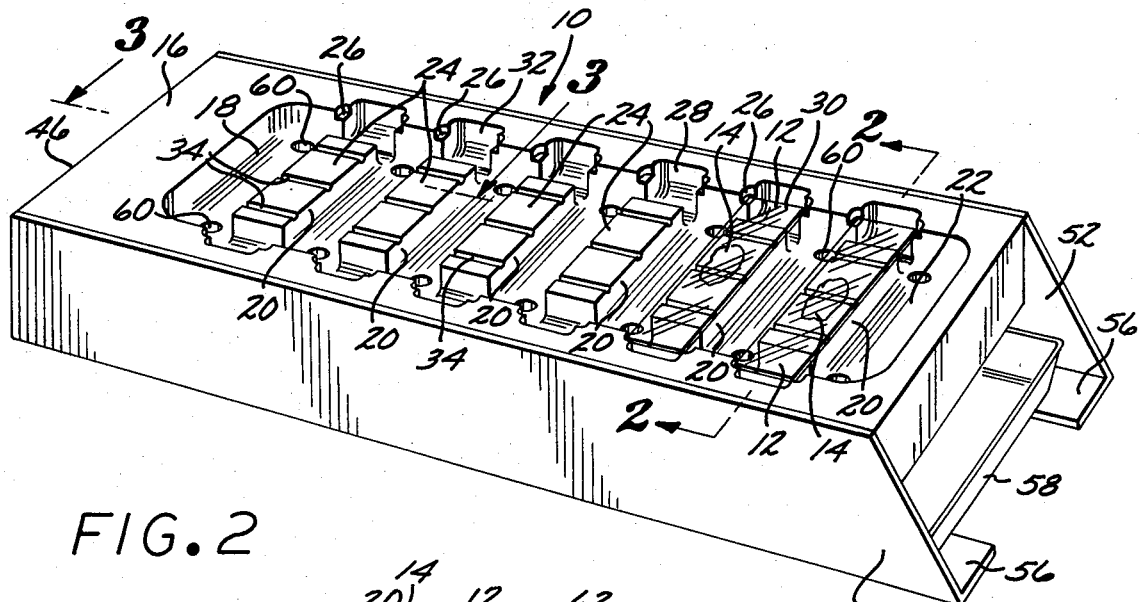
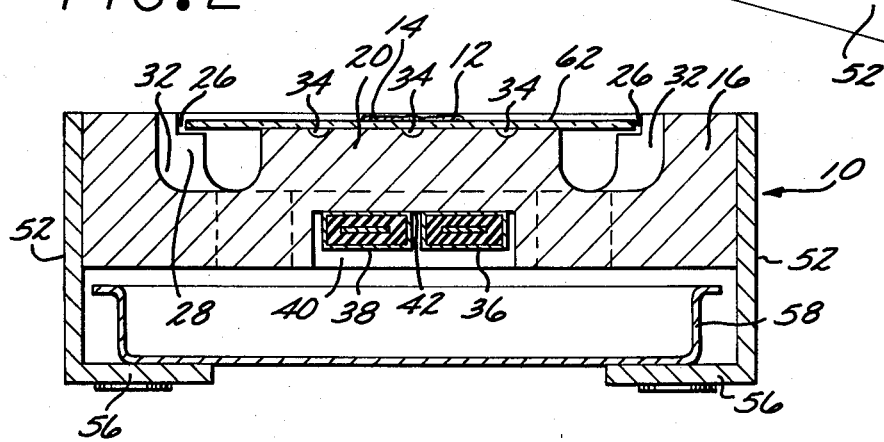
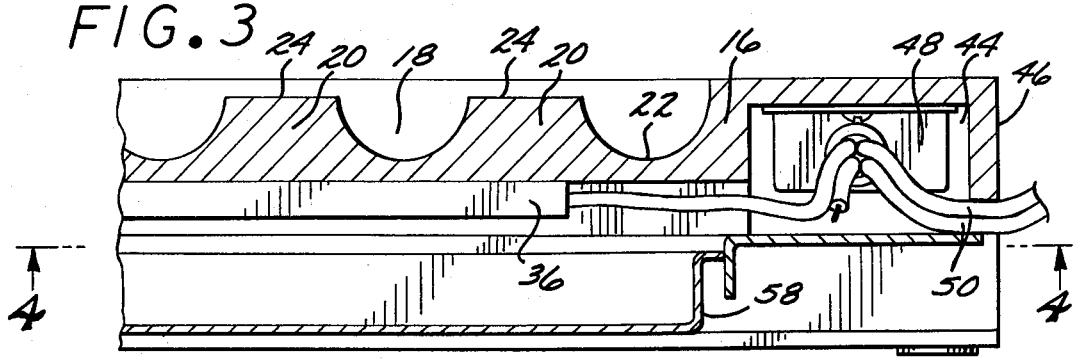
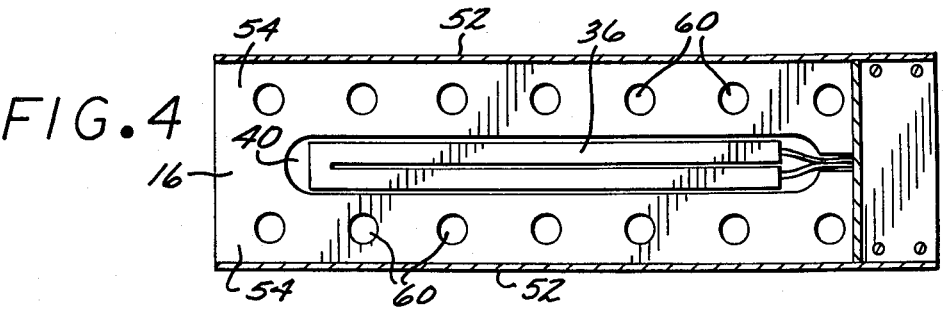

INCUBATING DEVICE FOR SPECIMEN MOUNTED ON GLASS SLIDES IN IMMUNOASSAYS

BACKGROUND OF THE INVENTION

1. Field of the Invention

The present invention is directed to a device used in connection with incubating a tissue section, sample or specimen with a series of reagent or test solutions. More particularly, the present invention is directed to a device wherein an array of glass slides bearing the tissue sections, samples or specimen are aligned for receiving the reagents or test solutions and wherein the slides are incubated with the test solutions or reagents at an elevated temperature.

2. Brief Description of the Prior Art

Processes whereby the presence or absence of an antigen in a tissue section, sample or specimen is determined by application of an antigen specific antibody, and subsequent application of a series of further antibodies, reagents and rinse solutions, are well known in the medical diagnostical and related arts.

In a typical process of the above-noted type, a tissue section, sample or specimen is fixedly mounted to a glass or microscope slide. Thereafter, several antibody and reagent solutions are successively applied to the slide by a pipette or dropper so that the respective antibody or reagent solution covers the tissue section or sample on the slide. Usually, the tissue section or sample is allowed to stand, i.e., is incubated, with the antibody or reagent solution for a predetermined amount of time. Furthermore, after the requisite incubation with each antibody or reagent is completed, the antibody or reagent solution is usually washed off the slide by application of a suitable rinsing solution. Various buffer solutions, or occasionally pure solvents such as water, are used for this purpose.

It is well known by those skilled in the art that in research and diagnostic laboratories and like places, several hundreds of the above-noted tests or assays may be performed daily. Therefore, in order to reduce the overall cost of the tests or assays, speed and convenience in handling of the slides and reagent solutions is of paramount importance.

In a copending application filed simultaneously with the present application for patent, and assigned to the same assignee as the present application, an improved process is described under the title "Improved Process for Immunoassaying Tissue Sections, Samples and the Like for the Presence of a Specific Antigen." A characteristic feature of the process disclosed in said copending application is that the several steps of incubation are performed at a higher than ambient temperature, preferably between 30°–50° C.

Thus, there is a definite need in the art for an incubating device which is adapted for heating the microscope slides in the above-noted incubation steps and which renders relatively convenient the manipulation of a plurality of slides used in the test or assay.

SUMMARY OF THE INVENTION

Accordingly it is an object of the present invention to provide an incubating device wherein a plurality of glass or microscope slides are arranged in an array to receive the respective antibody, reagent and rinsing solutions.

It is another object of the present invention to provide an incubating device wherein a plurality of glass or microscope slides are arranged in an array and are incubated with the respective antibody and reagent solutions at a higher than ambient temperature in a predetermined temperature range.

These and other objects and advantages are attained by an incubating device having a main body which preferably includes a recess substantially forming a tray in the main body. A plurality of substantially regularly spaced metal blocks are disposed in the recess, with each block having a substantially flat, substantially horizontally disposed surface. The surface of each block is adapted to receive and be in contact with at least a major portion of a respective glass or microscope slide.

An electrically powered heater is disposed below the main body, substantially below the metal blocks so as to heat the main body including the metal blocks. Thereby heat is eventually transferred from the metal blocks to the glass or microscope slides.

A thermostat or like temperature sensing and control device is mounted to the main body to sense the temperature of the same, and to control the output of the heater whereby the temperature of the metal blocks is kept substantially within a predetermined temperature range.

The features of the present invention can be best understood together with further objects and advantages by reference to the following description, taken in connection with the accompanying drawings.

BRIEF DESCRIPTION OF THE DRAWINGS

FIG. 1 is a perspective view of the incubating device of the present invention;

FIG. 2 is a cross-sectional view of the incubating device of the present invention, the cross section being taken on lines 2,2 of FIG. 1;

FIG. 3 is a partial cross-sectional view of the incubating device of the present invention, the cross section being taken on lines 3,3 of FIG. 1, and FIG. 4 is yet another cross-sectional view of the incubating device of the present invention, the cross section being taken on lines 4,4 of FIG. 3.

DESCRIPTION OF THE PREFERRED EMBODIMENT

The following specification taken in conjunction with the drawings set forth the preferred embodiment of the present invention in such a manner that any person skilled in the mechanical and electrical arts, can use the invention. The embodiment of the invention disclosed herein is the best mode contemplated by the inventors for carrying out their invention in a commercial environment, although it should be understood that various modifications can be accomplished within the parameters of the present invention.

Referring now to the drawing Figures, and particularly to the perspective view of FIG. 1, a preferred embodiment of the incubating device 10 of the present invention is disclosed.

It should be noted at the outset that the incubating device of the present invention is specifically adapted for use in a process wherein tissue sections, samples, specimen and the like are mounted on microscope slides 12, and wherein a series of test solutions or reagent solutions are successively applied to the slides 12, and are incubated with the samples or specimen 14 on the slides 12 for a predetermined time period at a higherthan-ambient temperature. In a specific immunoassay process for the practice of which the incubating device 10 is eminently suited, a desired temperature range wherein the aforesaid incubations take place, is between 30°-50° C. In fact, the most preferred temperature in the above-noted specific process is 37° C. This is described in the above-cross-referenced patent application. Nevertheless, it should be expressly understood that the scope of the present invention is not limited by the specific nature of the assay process or by the actual temperature used, in conjunction with the incubating device 10.

The entire structure of the incubating device 10 of the present invention serves the purposes of conveniently positioning the slides for successive applications of test or reagent solutions, for intermediate rinsing of the slides 12 with suitable buffer solutions or the like, and incubating the samples or specimen on the slides 12 at an elevated temperature with the respective test or reagent solutions. The samples or specimen, most commonly comprising tissue sections, are indicated on FIG. 1 with the reference numeral 14. The test or reagent solutions are not shown.

The preferred embodiment of the incubating device 10 has an elongated substantially rectangular main body 16, which is constructed from a single block of metal. Stainless steel, or aluminum is well suited for this purpose.

The main body has a relatively deep, elongated, substantially rectangular, upwardly opening recess 18. As it can be readily seen in FIG. 1, the recess 18 forms a tray in the main body 16.

A plurality of metal blocks or protrusions 20 project upwardly from a bottom wall 22 of the recess 18. The metal blocks or protrusions 20 are substantially regularly spaced in the recess 18, and have a substantially flat, substantially horizontally disposed, substantially rectangular upper surface 24. As it is described in more detail below, the metal blocks 20 comprise heating elements. Their upper surfaces 24 support and directly transfer heat to the microscope slides 12. In the herein described preferred embodiment, six (6) metal blocks 20 are provided. Therefore, the herein described preferred embodiment of the incubating device 10 is adapted to receive and simultaneously incubate six (6) microscope slides 12, with each slide 12 bearing a sample or specimen 14.

In order to properly align each microscope slide 12 relative to a respective metal block 20, a plurality of spaced notches 26 are provided in a sidewall 28 of the main body 16 which surrounds the tray forming recess 18. The notches 26 are positioned in the sidewall 28 so as to respectively accommodate the four corners 30 of the microscope slides 12. However, as is shown on the cross-sectional view of FIG. 2, the slides 12 rest solely on the flat upper heating surfaces 24 of the metal blocks 20. When properly positioned, the slides 12 do not come into contact with the sidewall 28 of the main body 16.

An additional notch 32 is provided in the sidewall 28 in association with each pair of the spaced aligning notches 26. The additional notches 32 allow convenient placement and removal of the slides 12 from the incubating device 10.

A plurality of grooves 34, preferably of a semicircular cross section, are disposed in the upper heating surface 24 of each metal block 20. The grooves 34 run substantially transverse to the longitudinal axes of the respective rectangular heating surfaces 24 and are substantially evenly spaced relative to one another. The purpose of the grooves 34 is to allow a liquid (not shown) trapped between the microscope slide 12 and flat heating surface 24 to quickly drain into the recess 18. This prevents adherence of the microscope slide 12 to the heating surface 24 due to the surface tension of the liquid (not shown).

Referring now to FIGS. 2-4, a heater 36 is shown mounted to the main body 16 below the recess 18. The heater 36 is an electrically operated resistance type heater well known in the art. An outer metal housing 38 of the heater 36 runs substantially along the entire length of the tray forming recess 18. The heater 36 is mounted into a flat bottomed second recess 40 which is formed in the main body 16, directly below the first recess 18. The second recess 40 is best shown in FIGS. 2 and 4.

The housing 38 of the heater 36 is in direct contact with a wall 42 of the second recess 40 so that heat is directly transferred from the heater 36 to the entire metal block of the main body 16. Thus, heat is transferred by direct conductance through the main body 16 to the metal blocks 20 which comprise the direct heating elements for the slides 12.

As is best shown on FIG. 3, yet a third recess or cavity 44 is formed in the main body 16 substantially adjacent to an end 46 of the main body 16. A temperature sensing or control device or thermostat 48 is mounted within the cavity 44. During operation of the incubating device 10, the thermostat 48 continuously senses the temperature of the main body 16.

The thermostat 48 is operatively coupled to the heater 36 to control the output of the heater 36 in response to the temperature of the main body 16. A cable or wire connecting the thermostat 48 with the heater 36, and also leading to a conventional electric outlet (not shown) is illustrated on FIGS. 3 and 4, and bears the reference numeral 50. In the herein described preferred embodiment, the thermostat 48 is preset during manufacture or assembly to maintain the temperature of the main body 16 in a predetermined temperature range. Preferably, the thermostat 48 is preset to maintain the temperature of the main body 16, including the temperature of the metal blocks 20, substantially at 37° C. Since the internal structure of the thermostat 48 is conventional, it is not deemed necessary to describe the thermostat 48 in detail.

Referring now to FIGS. 1-3, a pair of side plates 52 of the incubating device 10 of the present invention are shown. Each of the side plates 52 is mounted to a respective opposite side 54 of the main body 16 by soldering, welding or by screws (not shown). Each of the side plates 52 has a flange or lip 56 which is disposed substantially at a right angle to the side plate 52 itself. The flanges or lips 56 directly support the incubating device 10 on a support surface such as a laboratory bench (not shown).

A tray 58 is slideably and removably mounted on the flanges 56 to be disposed below the recess 18 of the main body 16. The tray 58 is best shown on FIGS. 1-3.

A plurality of holes or apertures 60 having substantially vertically disposed axes are provided in the main body 16, leading from the recess 18 to an area located directly above the tray 58. The purpose of the apertures 60 is to allow liquid to drain from the recess 18 into the tray 58, wherefrom the liquid may be removed from time to time.

Utilization of the above-described incubating device 10 in the above-noted immunoassay or like process should already be apparent to those skilled in the art from the foregoing description and from an inspection of the drawing Figures. Thus, the microscope slides 12 bearing the tissue sections, samples or specimen 14 are positioned on the upper heating surfaces 24 of the metal blocks 20. Each corner of each slide is disposed in an aligning notch 26. A sample or specimen 14 bearing surface 62 of each slide 12 is disposed upwardly, and not in contact with the heating surface 24. For the sake of clearly illustrating the structure of the incubating device 10, only two (2) slides 12 are shown on FIG. 1, although the herein described preferred embodiment of the device 10 may receive six (6) slides 12.

The liquid test or reagent solutions (not shown) are successively applied to the upper surfaces 62 of the slides 12, and are allowed to remain on the slides 12 for the respective predetermined time periods. The entire main body 20 of the incubating device 10 is maintained in the predetermined desired temperature range though the operation of the heater 36 which is controlled by the thermostat 48. Because direct transfer of heat from the metal blocks 20 to the slides 12 is highly efficient, the slides 12 and the reagent solutions (not shown) thereon are also substantially maintained in the predetermined temperature range.

After the predetermined time period for incubation with the respective reagent solution (not shown) is completed, the slides 12 are washed with a suitable rinsing solution or buffer (not shown). The slides are preferably not removed from the device 10 for the washing or rinsing step. Liquid (not shown) which would otherwise accumulate in the recess 18, is drained into the tray 58 through the apertures 60.

The grooves 34 in the upper heating surfaces 24 of the metal blocks 20 prevent substantial adherence of the slides 12 to the heating surfaces 24 by surface tension of any liquid which might otherwise be trapped between the slides 12 and the respective heating surfaces 24. Therefore, upon completion of the assay, the slides 12 are readily lifted off the metal blocks 20 and are removed from the device 10.

Several modifications of the above-described incubating device 10 may become apparent to those skilled in the art in light of the above disclosure. Therefore, the scope of the present invention should be interpreted solely from the following claims.

What is claimed is:

1. A device particularly adapted for warming a plurality of glass slides bearing a tissue culture, sample, specimen and the like, the device comprising:
   a main body comprising heat conducting material;
   a plurality of metallic heating members mounted to the main body, each heating member having a substantially horizontally disposed substantially flat heating surface adapted and dimensioned to be in direct contact with at least a major portion of the surface of one of the glass slides;
   aligning means mounted in the main body for aligning the plurality of glass slides to form an array, with each glass slide in the array having at least the major portion of its surface in direct heat exchange contact with the substantially flat heating surface of a respective heating member;
   a heater mounted in the main body and being adapted for heating the metallic heating members, and
   sensing and control means mounted in the main body and operatively connected with the heater for sensing the temperature of the main body and controlling the heater in response thereto, thereby keeping the heating members and the main body substantially at a predetermined temperature.

2. The invention of claim 1 wherein a recess is incorporated in the main body, and the heating members are mounted in the recess, a tray is slideably mounted in the main body to be normally disposed below the heating members, and wherein at least one opening is incorporated in the main body, said opening leading from the recess to the tray, whereby any liquid accumlated in the recess flows by gravitational flow into the tray.

3. The invention of claim 1 wherein the substantially flat surface of each of the heating members incorporates a plurality of grooves allowing a liquid caught between the surface of the heating members and respective glass slide to rapidly run off the flat surface, thereby substantially preventing adherence of the glass slides to the flat surfaces of the heating members and permitting their easy removal.

4. The invention of claim 1 wherein a recess is incorporated in the main body, and the heating members are mounted in the recess and wherein the main body includes a sidewall substantially surrounding the recess, said sidewall having a plurality of notches, the notches comprising the aligning means.

5. The invention of claim 1 wherein the main body comprises a unitary block of metal, said block of metal including the heating members.

6. A device adapted for aligning and heating an array of a plurality of substantially identically sized glass slides bearing a tissue culture, sample, specimen and the like, the device comprising:
   a main metal body of unitary construction from a single block of metal, and having an upwardly opening recess, the recess substantially forming a tray within the main metal body;
   a substantially regularly spaced array of upward protrusions from the recess in the main body, each protrusion comprising a heating element and having a substantially horizontally disposed substantially flat upper surface which is adapted to be in direct contact with a least a major portion of the surface of a respective glass slide when the slide is aligned and positioned in the device;
   an array of substantially regularly spaced aligning means provided in the main body for aligning and positioning the glass slides relative to the respective heating elements;
   a resistance heater mounted under the main body to be disposed in direct contact with the main body substantially directly underneath the heating elements, whereby heat is directly conducted from the resistance heater to the metal block of the main body and to the heating elements, and
   sensing and controls means operatively associated with the main body and with the resistance heater for sensing the temperature of the main body and controlling an output of the resistance heater to keep the temperature of the main body substantially in a predetermined temperature range.

7. The invention of claim 6 wherein a pair of side plates are mounted to the main body, and a tray is slideably and removably mounted to the side plates to be disposed substantially below the recess of the main body; and wherein at least one opening is provided in the recess through the main body and leading to the tray whereby liquid is drained by gravitational flow from the recess into the tray.

8. The invention of claim 6 wherein a wall of the main body surrounds the recess, and wherein the aligning means comprise a plurality of regularly spaced notches disposed in the wall.

9. The invention of claim 6 wherein each heating element has a plurality of regularly spaced grooves in the upper surface thereof, the grooves comprising means for allowing liquid trapped between the glass slide and the upper surface to escape and drain into the recess.

10. A device adapted for positioning and incubating at an elevated temperature a plurality of glass slides having a tissue section, sample, specimen and the like mounted thereon with a test reagent, antibody solution and the like which is added as a few drops of liquid to substantially cover the tissue section, sample or specimen on the glass slide, the device comprising:

a main body of unitary metal construction, said main body having an upwardly open recess forming a substantially elongated tray in the main body;

a plurality of substantially regularly spaced elongated metal blocks protruding upward from a bottom wall of the recess, the elongated metal blocks being disposed substantially transversely to a longitudinal axis of the elongated tray, each metal block having a substantially rectangular, substantially flat, substantially horizontally disposed upper surface adapted to be in contact with a major portion of a respective glass slide;

a resistance heater mounted to the main body substantially below the recess in the main body and in direct contact with the main body whereby heat is directly transferred from the resistance heater to the main body including the metal blocks, and temperature sensing and control means operatively associated with the main body for continuously sensing the temperature of the same, and with the resistance heater for controlling an output of the resistance heater in response to said sensed temperature, whereby the temperature of the metal block is kept substantially within a predetermined temperature range, and collecting means mounted below the main body for receiving and collecting liquid which may be first collected in the recess, said collecting means being in fluid communication with the recess through at least one aperture provided in the main body.

11. The invention of claim 10 wherein a wall of the main body substantially surrounding the recess includes means for positioning substantially rectangularly shaped glass slides relative to the respective metal blocks.

12. The invention of claim 11 wherein the means for positioning comprise a plurality of substantially regularly spaced notches in the wall of main body, the notches being adapted to accommodate respective corners of the glass slides.

13. The invention of claim 12 wherein the upper surface of each metal block has a plurality of grooves, the grooves comprising means for permitting escape of liquid which may be trapped between the glass slide and the upper surface.

14. The invention of claim 13 wherein a pair of substantially parallel disposed sidewalls are mounted to respective opposite sides of the main body, and wherein the collecting means comprise a tray slideably mounted to the sidewalls.

* * * * *